United States Patent
Kuzmanovic (10) Patent No.: US 7,940,886 B2
(45) Date of Patent: May 10, 2011

(54) 3D MEDICAL ANATOMICAL IMAGE SYSTEM USING 2D IMAGES

(75) Inventor: Miljan Kuzmanovic, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/568,986

(22) Filed: Sep. 29, 2009

(65) Prior Publication Data
US 2010/0086099 A1  Apr. 8, 2010

Related U.S. Application Data

(60) Provisional application No. 61/102,387, filed on Oct. 3, 2008.

(51) Int. Cl.
*A61B 6/00* (2006.01)
(52) U.S. Cl. ................................. 378/8; 378/4
(58) Field of Classification Search ............... 378/4, 8
See application file for complete search history.

(56) References Cited

U.S. PATENT DOCUMENTS

| | | | |
|---|---|---|---|
| 6,307,910 B1 * | 10/2001 | Acharya et al. | 378/4 |
| 6,522,712 B1 * | 2/2003 | Yavuz et al. | 378/4 |
| 6,535,570 B2 * | 3/2003 | Stergiopoulos et al. | 378/8 |
| 6,639,965 B1 * | 10/2003 | Hsieh et al. | 378/8 |
| 6,781,591 B2 | 8/2004 | Raskar | |
| 6,836,529 B2 * | 12/2004 | Li et al. | 378/8 |
| 7,505,549 B2 | 3/2009 | Ohishi et al. | |
| 2002/0156368 A1 | 10/2002 | Ohishi et al. | |
| 2002/0181645 A1 * | 12/2002 | Bruder et al. | 378/8 |
| 2005/0069081 A1 * | 3/2005 | Kokubun et al. | 378/15 |
| 2005/0152493 A1 * | 7/2005 | Seto | 378/20 |
| 2009/0021614 A1 | 1/2009 | Baker et al. | |

* cited by examiner

*Primary Examiner* — Edward J Glick
*Assistant Examiner* — Alexander H Taningco
(74) *Attorney, Agent, or Firm* — Alexander J Burke (57) ABSTRACT

A medical imaging system generates 3D anatomical images from acquired 2D anatomical images. The system includes a synchronization processor for providing a synchronization signal identifying a particular phase of heart operation of a particular patient. An image acquisition device acquires 2D anatomical images of a patient heart in angularly variable imaging planes over multiple different heart cycles at the particular phase of heart operation in response to the synchronization signal and in response to recorded data indicating imaging previously being performed at particular imaging plane angles. An image processor stores the recorded data to prevent imaging overlap at the particular imaging plane angles and to prevent unnecessary radiation exposure of the patient. The image processor processes 2D images acquired by the image acquisition device of the patient heart in multiple different imaging planes having relative angular separation, to provide a 3D image reconstruction of the patient heart.

18 Claims, 12 Drawing Sheets

| Angle | Pass 1 | Pass 2 | Pass 3 | Pass 4 |
|---|---|---|---|---|
| -98.6 | No coverage | New exposure | Overlap exposure | No coverage |
| -97.8 | No coverage | New exposure | Overlap exposure | No coverage |
| -97 | No coverage | New exposure | Overlap exposure | No coverage |
| -96.2 | No coverage | New exposure | Overlap exposure | No coverage |
| -95.4 | New exposure | Overlap exposure | No coverage | No coverage |
| -94.6 | New exposure | No coverage | No coverage | No coverage |
| -94.5 | No coverage | New exposure | No coverage | No coverage |
| -93.7 | New exposure | Overlap exposure | No coverage | No coverage |
| -92.9 | New exposure | Overlap exposure | No coverage | No coverage |

3D MEDICAL ANATOMICAL IMAGE SYSTEM USING 2D IMAGES

This is a non-provisional application of provisional application Ser. No. 61/102,387 filed Oct. 3, 2008, by M. Kuzmanovic.

FIELD OF THE INVENTION

This invention concerns a medical imaging system for generating 3D anatomical images from acquired 2D anatomical images by adaptively inhibiting imaging radiation emission and image acquisition to prevent imaging overlap at particular imaging plane angles and unnecessary radiation exposure of a patient.

BACKGROUND OF THE INVENTION

In known imaging systems, during medical imaging examination there are angles at which X-ray exposure is not performed (or not performed using high intensity X-ray beams) and this lack of data may prevent 3D image reconstruction from 2D images or reduce quality of a 3D image reconstruction. In order to avoid this, multiple imaging passes are performed in order to try to cover spatial and angular gaps and obtain exposure from almost all angles within a desired range. Known systems perform these additional imaging passes while performing radiation exposures during a rest phase of a heart indicated by an ECG signal. Each additional imaging pass is timed to start at a different point within a cardiac cycle to fill imaging spatial and angular gaps. However, duration of sequential heart cycles is not known and variable and need to be estimated. This potential inaccuracy, together with inaccuracies due to other disturbances in a normal hearth rhythm, results in either exposure overlaps or leftover spatial gaps in coverage. This may result in a patient receiving surplus X-ray exposure during overlap imaging and reduced image quality from gaps in angular coverage. A system according to invention principles addresses these deficiencies and related problems.

SUMMARY OF THE INVENTION

A system reduces X-ray exposure of a patient by eliminating spatially redundant imaging and increasing image quality in 2D image acquisition for 3D image volume reconstruction by eliminating gaps in angular coverage in ECG triggered rotational image acquisition, eliminating redundant acquisition and providing visual feedback of spatial coverage percentage during acquisition. A medical imaging system generates 3D anatomical images from acquired 2D anatomical images. The system includes a synchronization processor for providing a synchronization signal identifying a particular phase of heart operation of a particular patient. An image acquisition device acquires 2D anatomical images of a patient heart in angularly variable imaging planes over multiple different heart cycles at the particular phase of heart operation in response to the synchronization signal and in response to recorded data indicating imaging previously being performed at particular imaging plane angles. An image processor stores the recorded data to prevent imaging overlap at the particular imaging plane angles and to prevent unnecessary radiation exposure of the patient. The image processor processes 2D images acquired by the image acquisition device of the patient heart in multiple different imaging planes having relative angular separation, to provide a 3D image reconstruction of the patient heart

DETAILED DESCRIPTION OF THE INVENTION

A system reduces X-ray exposure of a patient by eliminating spatially redundant imaging and increasing image quality in 2D image acquisition for 3D image volume reconstruction by eliminating gaps in angular coverage in ECG triggered rotational image acquisition and eliminating redundant acquisition by monitoring and tracking a set of angles at which exposure has been performed. The system provides visual feedback of spatial coverage percentage during image acquisition. The system eliminates both overlaps and coverage gaps which reduces patient X-ray dosage and improves reconstructed 3D image volume quality. During a portion of an ECG cycle, the heart is relatively still. This fact is used by ECG triggered (or ECG gated) image acquisitions so that high intensity exposures are performed within this period and skipped or performed at lower radiation intensity outside of this period which advantageously reduces motion artifacts in a reconstructed 3D imaging volume dataset. High intensity exposures are not performed while the heart is in motion so spatial gaps in coverage are created. This means that there are angles at which exposures are not performed (or not performed using high intensity X-ray beams). Known systems view each radiation pass independently and typically perform redundant overlapping exposures (acquiring image frames) during the rest phase of a cardiac interval (part of the R-R interval) while the heart is relatively still.

Figure 1:
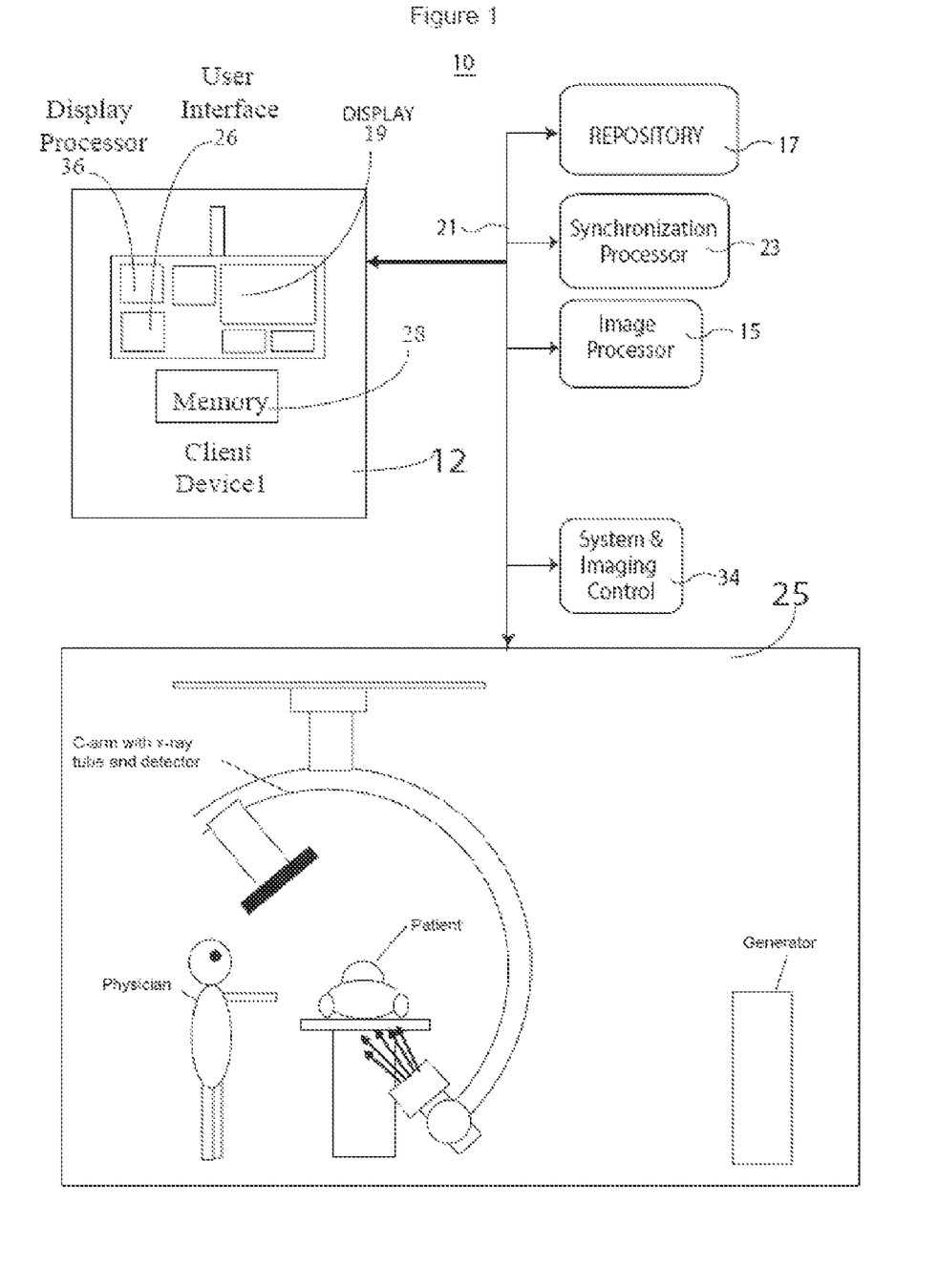
FIG. 1 shows a medical imaging system for generating 3D anatomical images from acquired 2D anatomical images, according to invention principles.

FIG. 1 shows medical imaging system 10 for generating 3D anatomical images from acquired 2D anatomical images. System 10 includes one or more processing devices (e.g., workstations, computers or portable devices such as notebooks, Personal Digital Assistants, phones) 12 that individually include memory 28, display processor 36, user interface 26 enabling user interaction with a Graphical User Interface (GUI) and display 19 supporting GUI and image presentation in response to predetermined user (e.g., physician) specific preferences. As well as device 12, system 10 also includes at least one repository 17, and imaging acquisition device 25 (e.g., an X-ray system), image processor 15, synchronization processor 23 and system and imaging controller 34, intercommunicating via network 21. At least one repository 17 stores medical image studies for patients in DICOM compatible (or other) data format. A medical image study individually includes multiple image series of a patient anatomical portion which in turn individually include multiple images.

Figure 2:
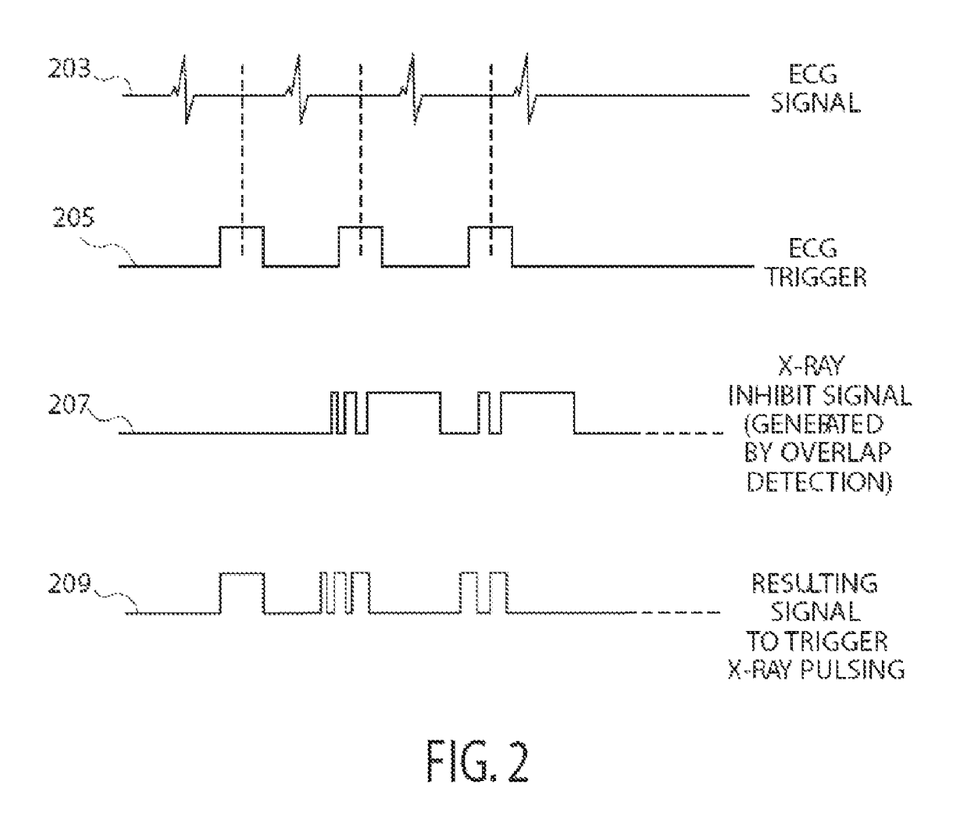
FIG. 2 shows generation of an inhibit signal to prevent imaging overlap at particular imaging plane angles and unnecessary radiation exposure of a patient, according to invention principles.
Figure 10:
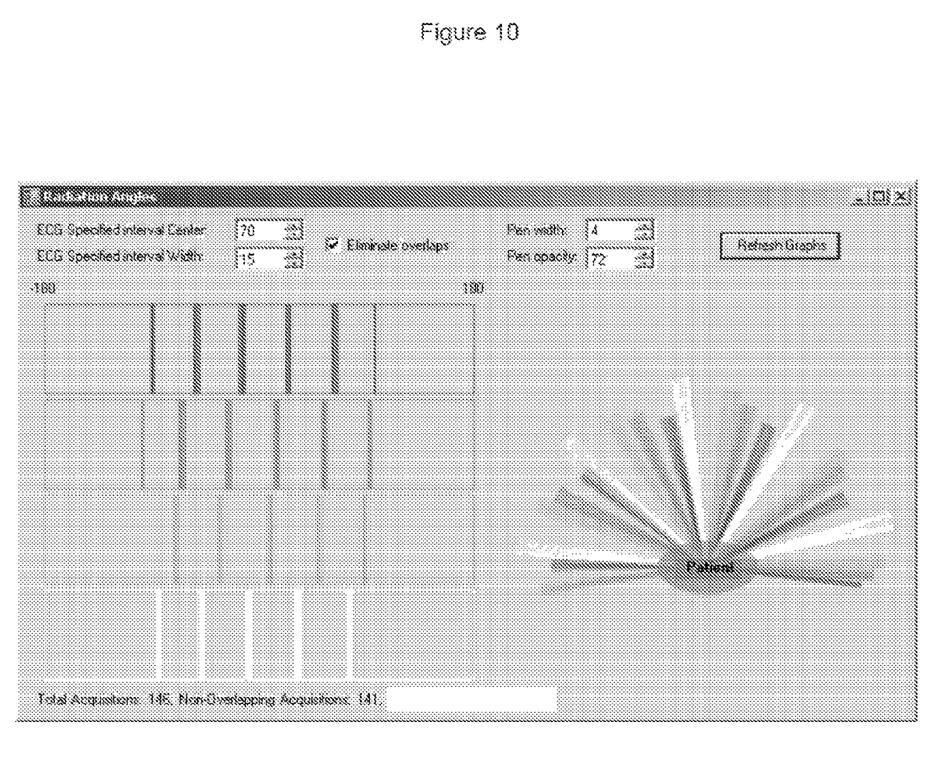
FIG. 10 shows rotational X-ray imaging angular coverage with a 70% cardiac phase center and 15% cardiac phase width with a nominal 3% overlap eliminated, according to invention principles.
Figure 11:
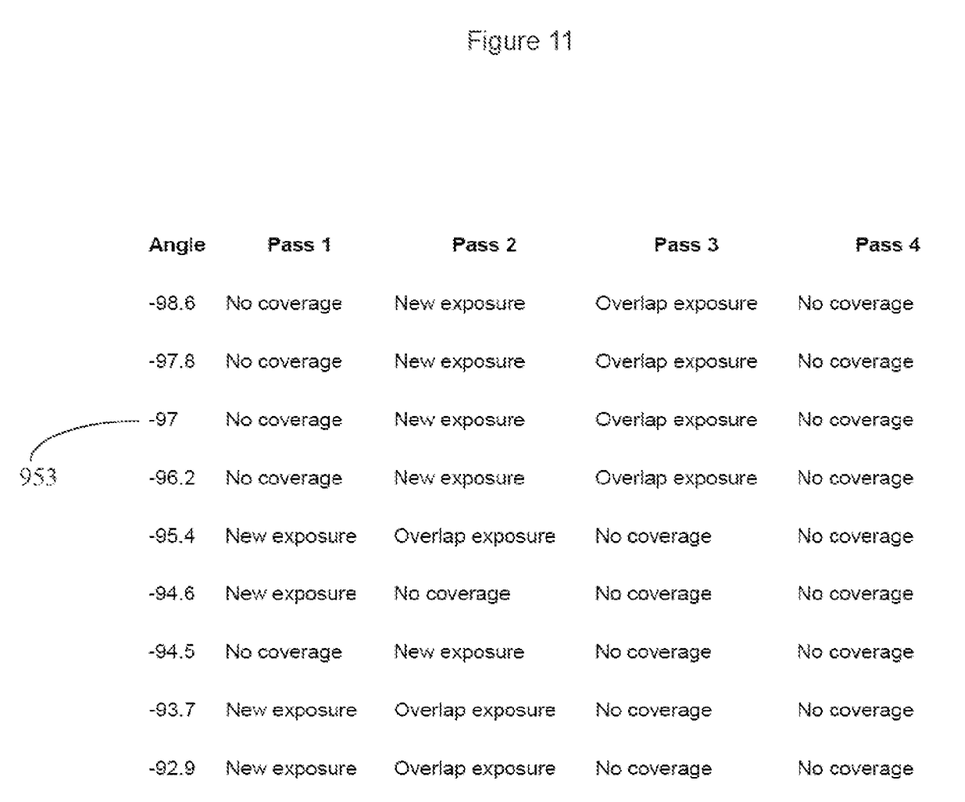
FIG. 11 shows a table recording data identifying new, overlap and zero exposure at particular X-ray system rotational angles, according to invention principles.

Synchronization processor 23 provides a synchronization signal identifying a particular phase of heart operation of a particular patient. Image acquisition device 25 acquires 2D anatomical images of a patient heart in angularly variable imaging planes over multiple different heart cycles at the particular phase of heart operation in response to the synchronization signal and in response to recorded data indicating imaging previously being performed at particular imaging plane angles. Image processor 15 stores the recorded data to prevent imaging overlap at the particular imaging plane angles and to prevent unnecessary radiation exposure of the patient. Image processor 15 processes 2D images acquired by the image acquisition device of the patient heart in multiple different imaging planes having relative angular separation, to provide a 3D image reconstruction of the patient heart FIG. 2 shows generation of an inhibit signal to prevent imaging overlap at particular imaging plane angles and unnecessary radiation exposure of a patient and also to fill angular gaps resulting from previous sequential imaging acquisitions. An ECG trigger signal 205 is generated from ECG signal 203 by synchronization processor 23 to encompass a heart rest phase, for example. Processor 23 analyzes recorded data in a table in repository 17 as exemplified by FIG. 11 to identify rotational angles where imaging acquisitions has been previously performed. Specifically, FIG. 11 shows a table identifying "New exposure", "Overlap exposure" and "No coverage" at particular X-ray system rotational angles over four imaging passes (Pass 1, 2, 3 and 4) comprising different sequences of image acquisitions performed at different times. FIG. 11 shows only a small portion of the imaging angles of an actual table to illustrate principle of operation. The table has one column identifying angles and one for each imaging pass of a C-arm of an X-ray imaging device 25 during image acquisition. Values "No coverage" indicates that while C-arm was at that angle the heart was not within the specified part of the ECG cycle, "New exposure" indicates that is was the first time an X-ray emission occurred at that angle, and "Overlap exposure" means that X-ray emission has already occurred at that angle (at least once). Tabular data of the form of FIG. 11 (but for more angles that are not shown) is used to generate the coverage diagrams of FIGS. 3-10. The FIG. 11 data represents acquisition within an interval of a heart cycle occupying 50% of an ECG indicated heart cycle interval and having a center at a 70% point from a cycle start point. An "Overlap exposure" has a "New exposure" to the left of it meaning that the "New exposure" was performed during a previous pass and this information is used to generate an "X-ray inhibit" signal.

Row 953 of FIG. 11 indicates for rotational angle -97 degrees there is no image acquisition ("No coverage") in imaging pass 1, a first image acquisition ("New exposure") in pass 2, an "Overlap exposure" in pass 3 and no image acquisition in pass 4, for example. Processor 23 determines from the data of FIG. 11 that an image is acquired in pass 2 at angle -97 degrees and that imaging pass 3 will produce an exposure overlap. In response to this determination, processor 23 derives an inhibit signal 207 using the table data of FIG. 11 to inhibit image acquisition at angle -97 degrees in imaging pass 3 to prevent overlap. Processor 23 logically combines signals 205 and 207 to derive synchronization signal 209 for use in acquiring an image at an angle of -97 degrees during imaging pass 2 and inhibiting acquisition in pass 3.

In one embodiment, system 10 performs image acquisition in response to a synchronization signal derived from an ECG (R peak). The synchronization signal incorporates different start delays for individual image acquisitions to cover gaps resulting from previous sequential imaging acquisitions. FIGS. 3-10 include two types of diagrams generated using the same data extracted from clinical image acquisition in 4 imaging passes of ECG gated rotational acquisition. Four diagrams on the left side (e.g., diagrams 303, 305, 307 and 309 FIG. 3) are linear type with -180 degrees of X-ray beam orientation on the far left side and +180 degrees of beam orientation on the far right side. Individual imaging passes 1-4 are rendered in a different gray shade (or color) in diagrams 303, 305, 307 and 309 and each image acquisition (exposure) is represented in a diagram with one vertical line. The polar type diagrams (e.g., diagram 313 FIG. 3) are patient centric polar diagrams with passes rendered together. X-ray beam direction is from the perimeter towards a patient 315. A zero degree position, an origin, is directly above the patient, -90 degrees is directly to the left of the patient, +90 directly to the right and -180 and +180 both directly below. In a polar diagram to facilitate pass and overlap identification, an individual imaging pass is rendered using a different radius and a different gray scale (color) so the same shade/color identifying different passes is used in both polar diagram 313 and linear diagrams 303, 305, 307 and 309.

Figure 3:
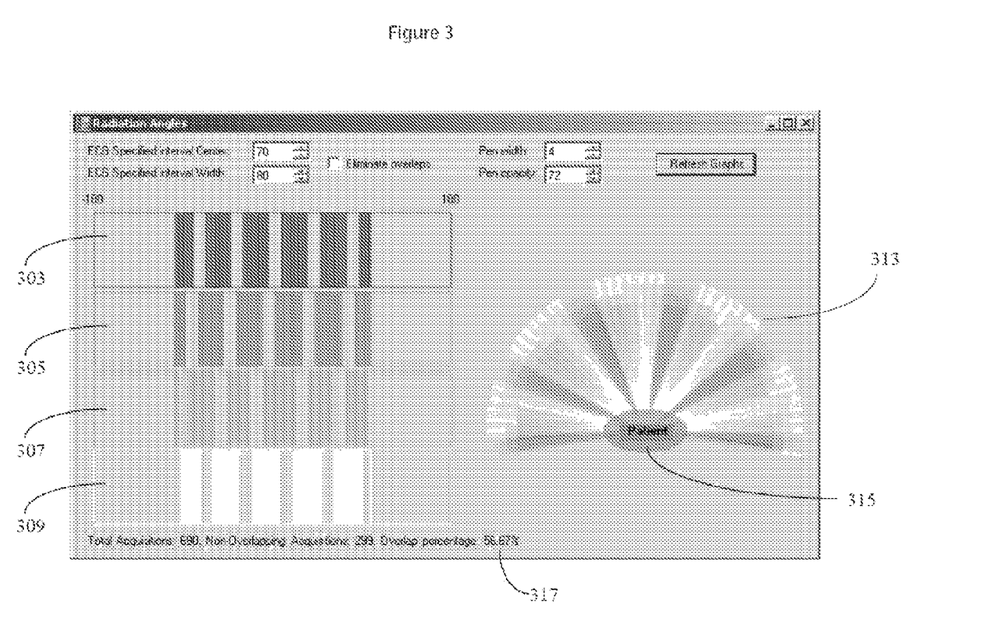
FIG. 3 shows rotational X-ray imaging angular coverage with a 70% cardiac phase center and 80% cardiac phase width indicating inherent overlap.
Figure 4:
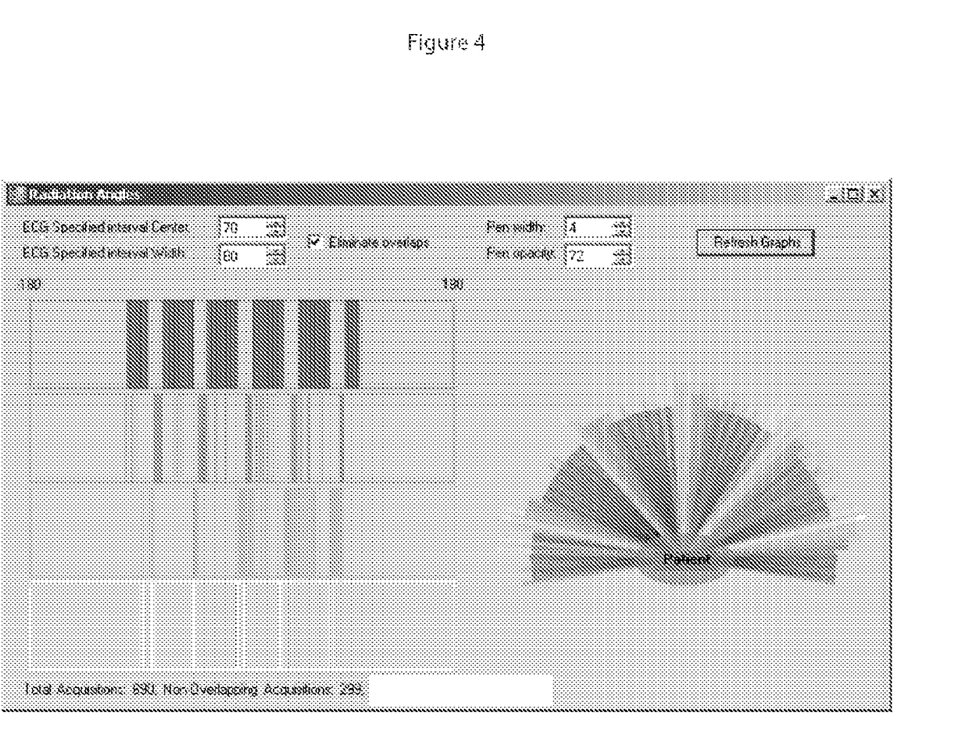
FIG. 4 shows rotational X-ray imaging angular coverage with a 70% cardiac phase center and 80% cardiac phase width without overlaps, according to invention principles.

FIG. 3 shows rotational X-ray imaging angular coverage performed without inhibiting overlap, acquired within an interval of a heart cycle occupying 80% of the cycle and having a center at a 70% point from a cycle start point. Linear diagrams 303, 305, 307 and 309 show four separate imaging passes respectively indicating complete angular coverage as there are no spaces between the four coverage diagrams. Polar diagram 313 similarly indicates overlap and complete coverage. The complete coverage ensures good image quality of a 3D reconstructed imaging volume dataset, but overlaps in coverage are indicated in element 317 as exceeding 56% resulting in redundant imaging and additional radiation dosage being received by the patient. In contrast, FIG. 4 shows rotational X-ray imaging angular coverage of FIG. 3 performed with image data processor 23 inhibiting the 56% overlap. Image data processor 23 analyzes dynamically recorded data generated substantially contemporaneously with each image acquisition that records "New exposure", "Overlap exposure" and "No coverage" at particular X-ray system rotational angles over four imaging passes of one acquisition process, for example as illustrated in FIG. 11. Processor 23 determines if an image has already been acquired in a previous pass at a particular rotational angle and generates an inhibit signal to prevent image acquisition at the particular angle in subsequent imaging passes. In response to this determination, processor 23 derives inhibit and synchronization signals (e.g., signals 207 and 209 respectively of FIG. 2) using the table data of FIG. 11 in order to inhibit redundant image acquisition (or to perform image acquisition at a reduced radiation level). Thereby the overlap coverage of FIG. 3 is substantially eliminated in FIG. 4 and radiation exposure of the patient is substantially reduced.

Figure 5:
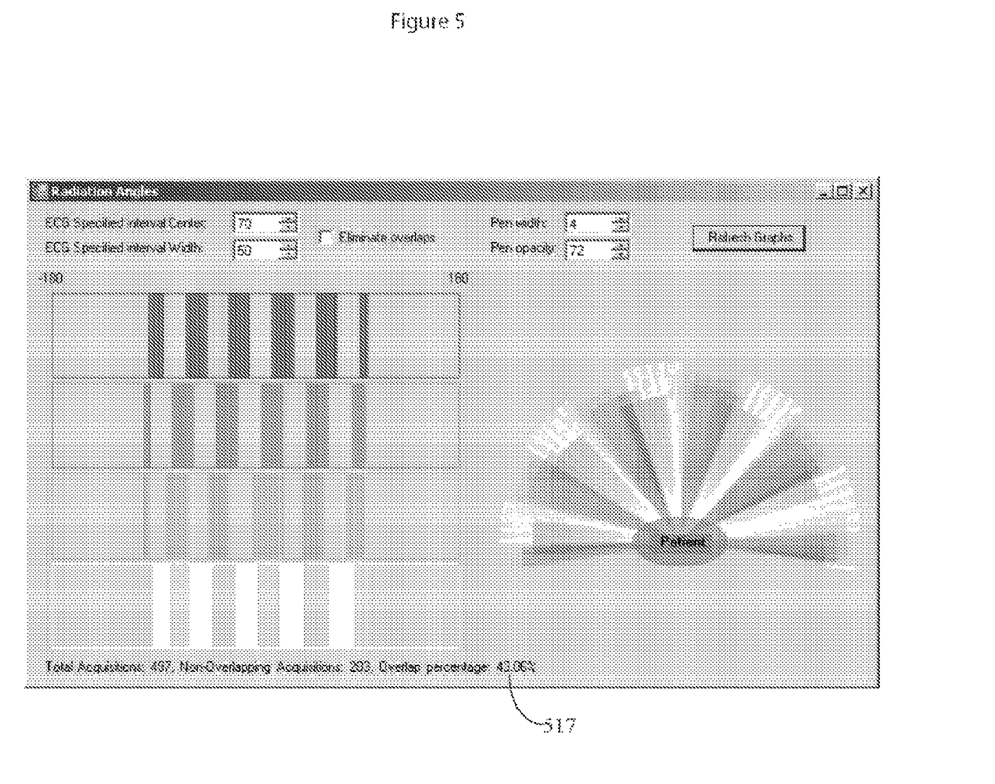
FIG. 5 shows rotational X-ray imaging angular coverage with a 70% cardiac phase center and 50% cardiac phase width indicating inherent overlap.
Figure 6:
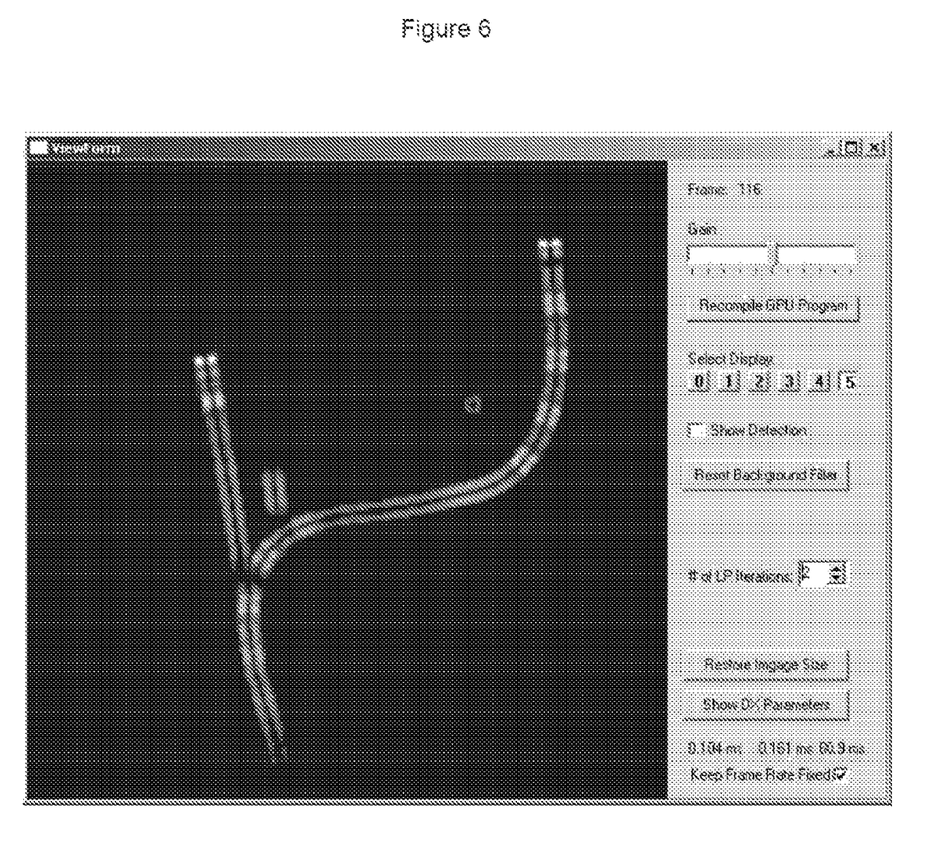
FIG. 6 shows rotational X-ray imaging angular coverage with a 70% cardiac phase center and 50% cardiac phase width without overlaps, according to invention principles.

FIG. 5 shows rotational X-ray imaging angular coverage performed without inhibiting overlap, acquired within an interval of a heart cycle occupying 50% of the cycle and having a center at a 70% point from a cycle start point. In order to reduce radiation dose, known systems can be set up to use a narrower cardiac interval (a narrower segment within an R-R cycle). In FIG. 5 a 50% cardiac interval is used instead of the 80% interval of FIGS. 3 and 4 and this reduces overlap to about 43% (item 517) and also reduces radiation dose. In contrast, FIG. 6 shows rotational X-ray imaging angular coverage of FIG. 5 performed with image data processor 23 inhibiting the 43% overlap. Image data processor 23 analyzes dynamically recorded data generated substantially contemporaneously with each image acquisition as previously described in connection with FIG. 4 and FIG. 11. Processor 23 determines if an image has already been acquired in a previous pass at a particular rotational angle and generates an inhibit signal to prevent image acquisition at the particular angle in subsequent imaging passes. In response to this determination, processor 23 derives inhibit and synchronization signals (e.g., signals 207 and 209 respectively of FIG. 2) using the table data of FIG. 11 to inhibit image acquisition (or to perform image acquisition at a reduced radiation level). Thereby the overlap coverage of FIG. 5 is substantially eliminated in FIG. 6 and radiation exposure of the patient is substantially reduced.

Figure 7:
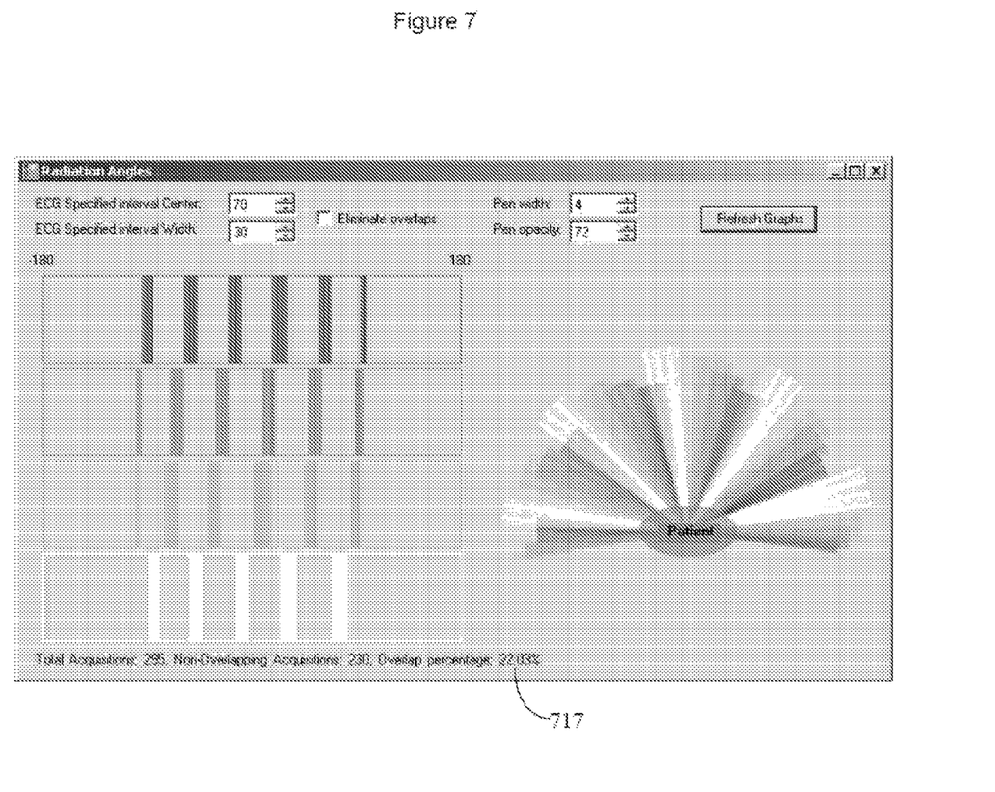
FIG. 7 shows rotational X-ray imaging angular coverage with a 70% cardiac phase center and 30% cardiac phase width with overlap.
Figure 8:
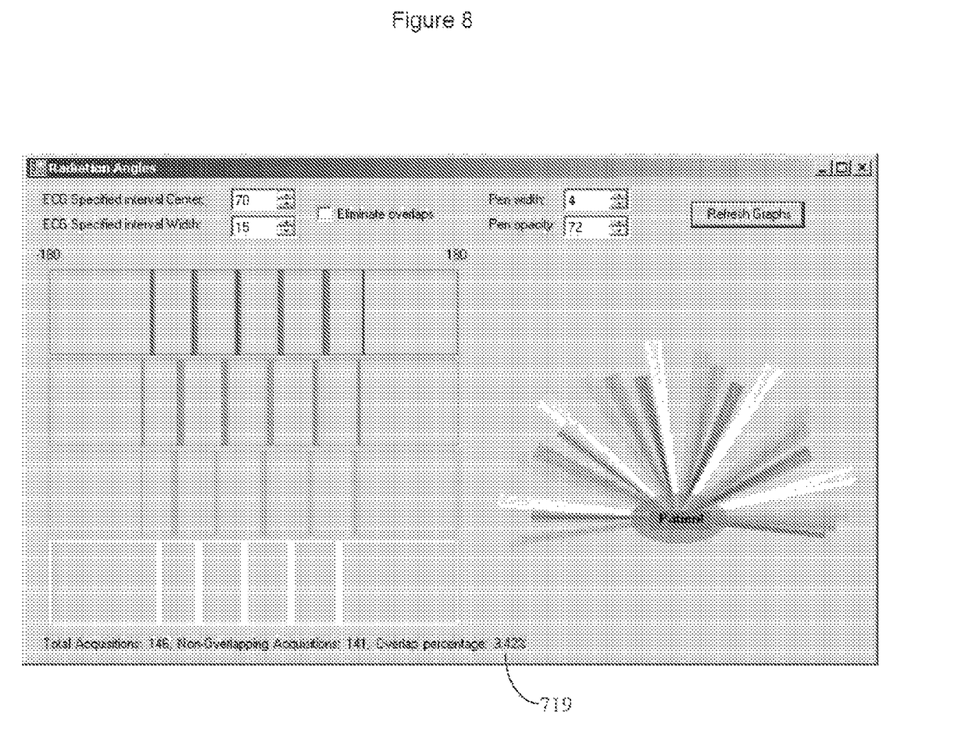
FIG. 8 shows rotational X-ray imaging angular coverage with a 70% cardiac phase center and 15% cardiac phase width with overlap.

FIG. 7 shows rotational X-ray imaging angular coverage performed without inhibiting overlap, acquired within an interval of a heart cycle occupying 30% of the cycle and having a center at a 70% point from a cycle start point. In FIG. 7 a 30% cardiac interval is used to reduce overlap to about 22% (item 717) and also reduce radiation dose by use of the narrower 30% cardiac interval (a narrower segment within an R-R cycle). FIG. 8 shows rotational X-ray imaging angular coverage performed without inhibiting overlap, acquired within an interval of a heart cycle occupying 15% of the cycle and having a center at a 70% point from a cycle start point. In FIG. 8 a 15% cardiac interval is used to reduce overlap to about 3% (item 719) and also reduce radiation dose. Such narrow cardiac interval widths are typically not used because they result in gaps in angular coverage. The gaps may be reduced by increasing the number of imaging passes performed, but this involves use of more contrast agent which may also reduce patient safety.

Figure 9:
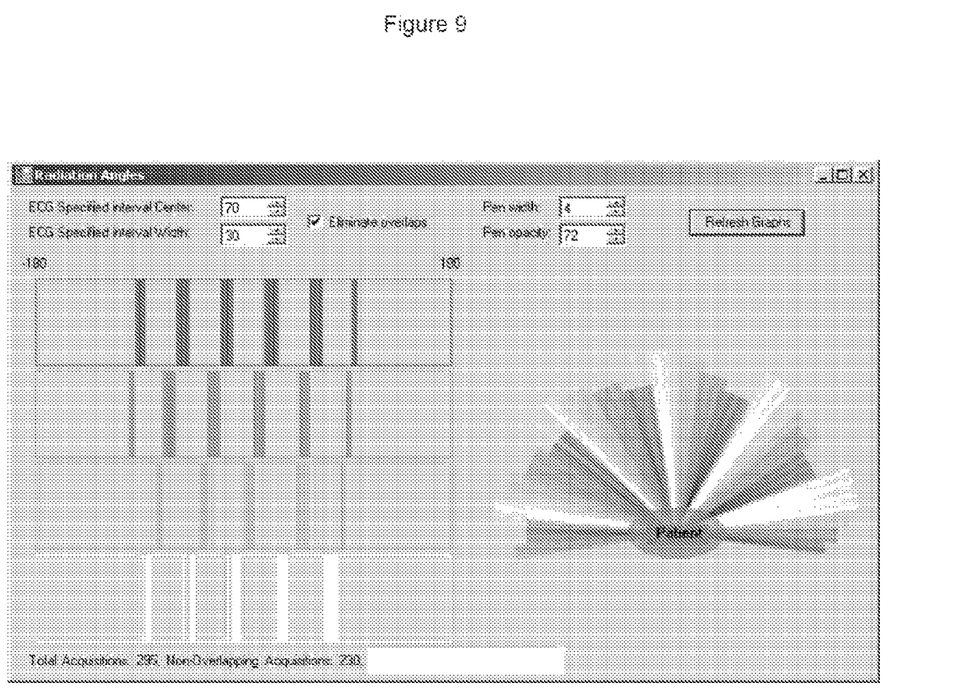
FIG. 9 shows rotational X-ray imaging angular coverage with a 70% cardiac phase center and 30% cardiac phase width with a nominal 22% overlap eliminated, according to invention principles.

FIG. 9 shows rotational X-ray imaging angular coverage performed with a nominal 22% overlap eliminated, acquired within an interval of a heart cycle occupying 30% of the cycle and having a center at a 70% point from a cycle start point. Similarly, FIG. 10 shows rotational X-ray imaging angular coverage performed with a nominal 3% overlap eliminated, acquired within an interval of a heart cycle occupying 15% of the cycle and having a center at a 70% point from a cycle start point. Image data processor 23 inhibits overlap in the acquisitions depicted in FIGS. 9 and 10 using inhibit and synchronization signals (e.g., signals 207 and 209 respectively of FIG. 2) derived using the table data of FIG. 11 as previously described in connection with FIGS. 2 and 5, for example. The system advantageously provides complete coverage with increased specified cardiac phase width, which results in higher image quality, while reducing patient radiation dose. Processor 23 processes the real-time (while image acquisition is under way) coverage information of FIG. 11 to provide a display of coverage information as feedback to a user indicating acquisition progress. In one embodiment, acquisition progress comprising coverage information is presented in graphical form like a pie chart or in a bar representing a numerical value with a range from 0% to 100% of coverage. A user seeing coverage reach 100% or close enough to achieve good image quality, is able to stop the acquisition and avoid performing more imaging passes. This additionally reduces the amount of contrast agent that is injected since overall acquisition time is reduced. In one embodiment, processor 23 automatically terminates image acquisition once coverage reaches 100% or substantially close to 100% (i.e., exceeding a predetermined threshold).

Figure 12:
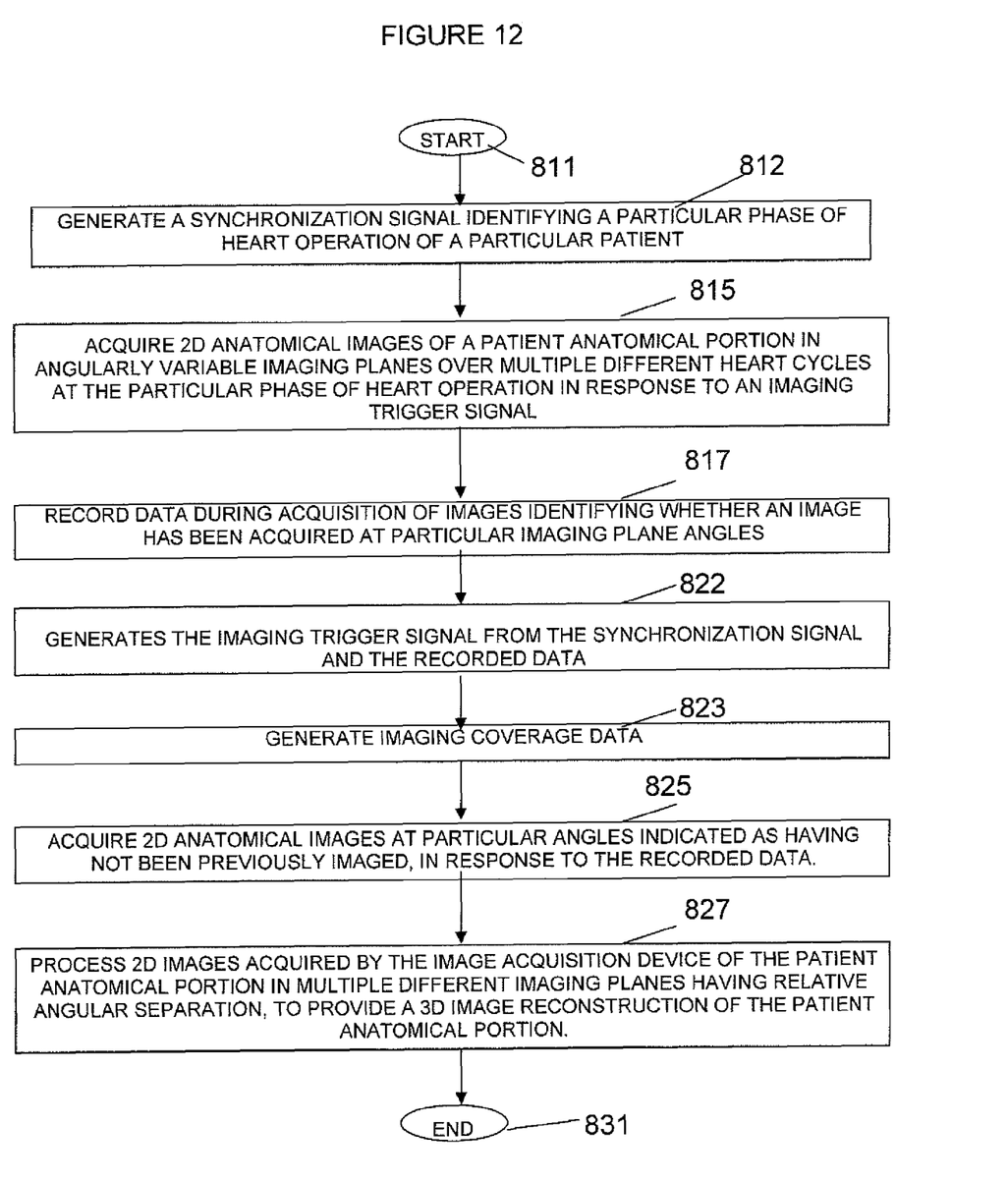
FIG. 12 shows a flowchart of a process used by a medical imaging system for generating 3D anatomical images from acquired 2D anatomical images, according to invention principles.

FIG. 12 shows a flowchart of a process used by a medical imaging system for generating 3D anatomical images from acquired 2D anatomical images. In step 812 following the start at step 811, synchronization processor 23 (FIG. 1) generates a synchronization signal identifying a particular phase of heart operation of a particular patient. Image acquisition device 25 in step 815 acquires 2D anatomical images of a patient anatomical portion (e.g., a heart) in angularly variable imaging planes over multiple different heart cycles at the particular phase of heart operation in response to an imaging trigger signal. Device 25 includes a rotational C-arm unit housing a radiation emitter and detector. The angularly variable imaging planes are variable in two or three dimensions. In step 817 image processor 15 records data during acquisition of images identifying whether an image has been acquired at particular imaging plane angles. The recorded data indicates at least one of, (a) an overlap imaging exposure, (b) a new imaging exposure and (c) no coverage, occurs at a particular imaging plane angle. In step 822, processor 15 generates the imaging trigger signal from the synchronization signal and the recorded data. The imaging trigger signal is for initiating and inhibiting image acquisition at particular imaging plane angles by image acquisition device 25 and preventing imaging overlap at the particular imaging plane angles and unnecessary X-ray radiation exposure of the patient.

In step 823 mage processor 15 uses the recorded data in generating imaging coverage data indicating proportion of an angular region imaged to show progress of image acquisition. Processor 15 initiates presentation of the imaging coverage data in graphical form comprising at least one of, (a) a polar chart, (b) a pie chart and (c) a bar chart, on display 19. In another embodiment, the imaging coverage data is presented in text form. Image processor 15 initiates image acquisition at particular angles as well as at particular angles indicated as having not been previously imaged and also with reduced exposure time to reduce patient radiation exposure, in response to the recorded data. Specifically, image acquisition device 25 in step 825 acquires 2D anatomical images at particular angles indicated as having not been previously imaged, in response to the recorded data. In step 827 image processor 15 processes 2D images acquired by image acquisition device 25 of the patient anatomical portion in multiple different imaging planes having relative angular separation, to provide a 3D image reconstruction of the patient anatomical portion. The process of FIG. 12 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-12 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system reduces spatially redundant image acquisition and eliminates both overlaps and coverage gaps by monitoring and tracking a set of angles at which exposure has been previously performed in image scanning passes and provides visual feedback of spatial coverage percentage during image acquisition. Further, the processes and applications may, in alternative embodiments, be located on one or more (e.g., distributed) processing devices on the network of FIG. 1. Any of the functions and steps provided in FIGS. 1-12 may be implemented in hardware, software or a combination of both.

What is claimed is:

1. A medical imaging system for generating 3D anatomical images from acquired 2D anatomical images, comprising:
   a synchronization processor for providing a synchronization signal identifying a particular phase of heart operation of a particular patient;
   an image acquisition device for acquiring discrete 2D anatomical images of a patient heart in angularly variable imaging planes over a plurality of different heart cycles at said particular phase of heart operation in response to said synchronization signal and in response to recorded data indicating imaging previously being performed at particular individual angles of a 2D imaging plane to prevent imaging overlap at said particular individual angles of a 2D imaging plane and to prevent unnecessary radiation exposure of said patient; and
   an image processor for,
      storing the recorded data, and
      processing 2D images acquired by said image acquisition device of said patient heart in a plurality of different imaging planes having relative angular separation, to provide a 3D image reconstruction of said patient heart.

2. A system according to claim 1, wherein
   said recorded data indicates a first exposure has previously been performed at a particular individual 2D imaging plane angle,
   said image processor derives an imaging trigger signal from said synchronization signal and said recorded data, said imaging trigger signal being for initiating and inhibiting image acquisition at particular individual angles of a 2D imaging plane by said image acquisition device and
   said angularly variable imaging planes are variable in two dimensions.

3. A system according to claim 1, wherein
   said angularly variable imaging planes are variable in three dimensions.

4. A system according to claim 1, wherein
   said recorded data indicates a first exposure and an overlap exposure has previously been performed at a particular individual 2D imaging plane angle and
   said image acquisition device for acquiring 2D anatomical images of a patient heart in angularly variable imaging planes includes a rotational C-arm unit housing a radiation emitter and detector.

5. A system according to claim 1, wherein said image processor records data indicating imaging being performed at particular individual angles of a 2D imaging plane during image acquisition.

6. A system according to claim 5, wherein
   said image processor records data indicating at least one of, (a) an overlap imaging exposure, (b) a new imaging exposure and (c) no coverage, occurs at a particular imaging plane angle.

7. A system according to claim 5, wherein
   said image processor generates imaging coverage data indicating imaging plane angles of an angular region where images have not been acquired and the proportion of the angular region imaged.

8. A system according to claim 7, wherein
   said imaging coverage data is presented in graphical form comprising at least one of, (a) a polar chart, (b) a pie chart and (c) a bar chart.

9. A system according to claim 7, wherein
said imaging coverage data is presented in text form.

10. A system according to claim 5, wherein
said image processor initiates image acquisition at particular angles in response to the recorded data.

11. A system according to claim 5, wherein
said image processor initiates image acquisition at particular angles with reduced exposure time to reduce patient radiation exposure, in response to the recorded data.

12. A system according to claim 5, wherein
said image processor initiates image acquisition at particular angles indicated as having not been previously imaged, in response to the recorded data.

13. An X-ray medical imaging system for generating 3D anatomical images from acquired 2D anatomical images, comprising;
a synchronization processor for providing a synchronization signal identifying a particular phase of heart operation of a particular patient;
an image acquisition device for acquiring discrete 2D anatomical images of a patient anatomical portion in angularly variable imaging planes over a plurality of different heart cycles at said particular phase of heart operation in response to said synchronization signal and in response to recorded data indicating imaging previously being performed at particular individual angles of a 2D imaging plane to prevent imaging overlap at said particular individual angles of a 2D imaging plane and to prevent unnecessary radiation exposure of said patient; and
an image processor for,
storing the recorded data during acquisition of images identifying whether an image has been acquired at particular imaging plane angles and processing 2D images acquired by said image acquisition device of said patient anatomical portion in a plurality of different imaging planes having relative angular separation, to provide a 3D image reconstruction of said patient anatomical portion.

14. A system according to claim 13, wherein
said image processor uses the recorded data in generating imaging coverage data indicating imaging plane angles of an angular region where images have not been acquired and the proportion of the angular region imaged to show progress of image acquisition.

15. A system according to claim 13, wherein
said image processor derives an imaging trigger signal from said synchronization signal and said recorded data, said imaging trigger signal being for initiating and inhibiting image acquisition at particular imaging plane angles by said image acquisition device and
said image processor initiates image acquisition at particular angles in response to the recorded data.

16. A system according to claim 13, wherein
said image processor initiates 2D image acquisition at particular individual angles indicated as having not been previously imaged, in response to the recorded data.

17. A method of X-ray medical imaging for generating 3D anatomical images from acquired 2D anatomical images, comprising the activities of:
generating a synchronization signal identifying a particular phase of heart operation of a particular patient;
acquiring discrete 2D anatomical images of a patient anatomical portion in angularly variable imaging planes over a plurality of different heart cycles at said particular phase of heart operation in response to an imaging trigger signal;
recording data during acquisition of images identifying whether an image has been acquired at particular individual 2D imaging plane angles;
generating said imaging trigger signal from said synchronization signal and the recorded data, said imaging trigger signal being for initiating and inhibiting image acquisition at particular individual angles of a 2D imaging plane by said image acquisition device and preventing imaging overlap at said particular imaging plane angles and unnecessary X-ray radiation exposure of said patient; and
processing 2D images acquired by said image acquisition device of said patient anatomical portion in a plurality of different imaging planes having relative angular separation, to provide a 3D image reconstruction of said patient anatomical portion.

18. A method according to claim 17, including the activity of
acquiring 2D anatomical images at particular individual angles indicated as having not been previously imaged, in response to the recorded data.

* * * * *